United States Patent [19]

Filhol

[11] Patent Number: 5,104,321

[45] Date of Patent: Apr. 14, 1992

[54] DENTAL POST AND METHOD

[76] Inventor: Stuart J. Filhol, Cuilin Cottage, Desertserges Enniskeane, Co.Cork, Eire, Great Britain

[21] Appl. No.: 436,542

[22] Filed: Nov. 14, 1989

[30] Foreign Application Priority Data

Nov. 16, 1988 [GB] United Kingdom ................ 8826823
Jul. 28, 1989 [GB] United Kingdom ................ 8917361

[51] Int. Cl.⁵ .............................................. A61C 5/08
[52] U.S. Cl. .................................... 433/221; 433/224
[58] Field of Search ................. 433/224, 221, 220, 81

[56] References Cited

U.S. PATENT DOCUMENTS

| 626,738 | 6/1899 | Underwood | 433/221 |
|---|---|---|---|
| 1,149,239 | 8/1915 | Williams | 433/221 |
| 1,612,227 | 12/1926 | Simmons | 433/221 |
| 4,334,865 | 6/1982 | Borle | 433/221 |
| 4,515,565 | 5/1985 | Winter-Moore et al. | 433/221 |
| 4,729,736 | 3/1988 | Weissman | 433/221 |

Primary Examiner—John J. Wilson
Attorney, Agent, or Firm—Ostrolenk, Faber, Gerb & Soffen

[57] ABSTRACT

A dental post 5 has a lower portion 4 that is fitted within a pre-prepared dental root canal 2, 3 and an upper portion 6 to which a dental crown 8 can be fitted. The root canal is provided with a plurality of projections 26 that extend downwardly and inwardly and the post, which is preferably tapered, and the lower portion of the post has a plurality of notches 16 that are preferably independent grooves that face upwardly. The post can then be secured substantially without screwing, by means of cement in the annulus 7 between the post and the canal. Preferably the lower portion of the post is tapered and has grooves or other notches that open upwardly and outwardly and the upper portion has grooves that open downwardly. The pitch of the grooves 16 in the lower portion is generally not more than 0.5 mm. The invention also includes a dental reamer that can be used to form a profiled cavity in a tooth and that has an elongated cutting head (30, 31, 32) having a plurality of cutting elements (34) that can be used for cutting into the wall of the canal to define the projections 26.

17 Claims, 2 Drawing Sheets

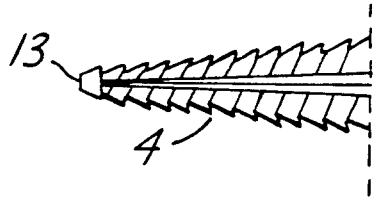
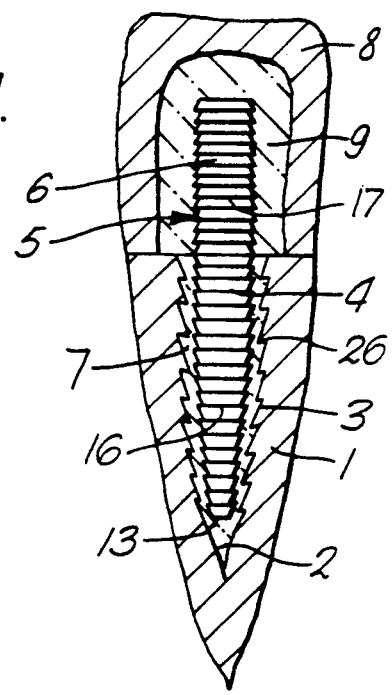
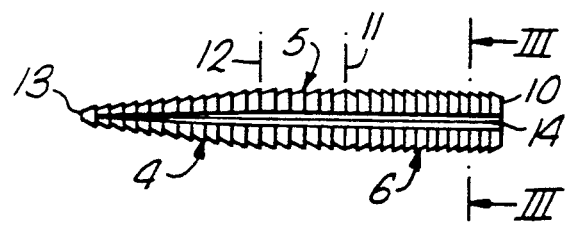
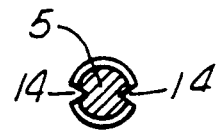
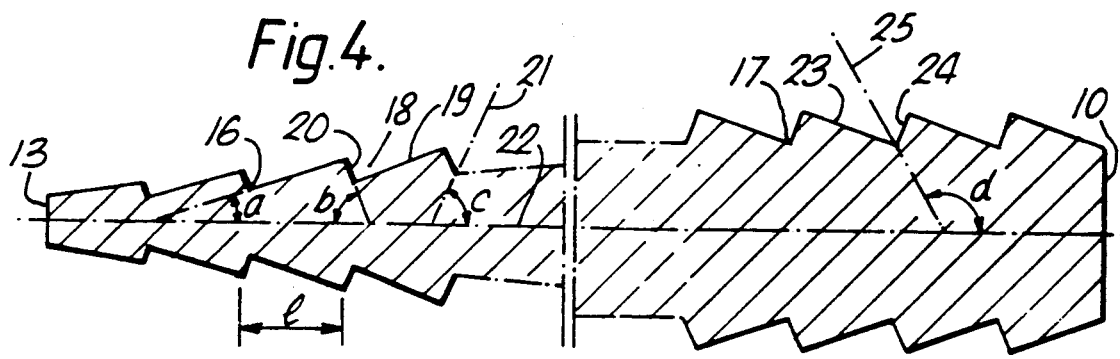
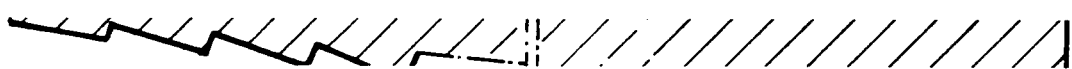

DENTAL POST AND METHOD

This invention relates to improved dental posts and methods for securing a dental crown above a root canal in order to provide a secure bond and thereby provide a cosmetically desirable permanent dental crown. The invention also relates to dental reamers.

A dental post has an upper portion to which a dental crown can be secured and a lower portion that can be secured within a dental root canal and that extends downwardly from the upper portion. In this specification I am using the words "upper" and "upwardly" to indicate the direction towards the crown and the words "downward" and "downwardly" to indicate the direction into the root canal. The root canal is drilled out to a depth and diameter sufficient to receive the chosen length of the lower portion of the post, the post is fitted within the drilled cavity and is bonded in position by a cement that fills the annulus between the surface of the lower portion and the inner surface of the cavity. The crown is then secured on to the upper portion.

The post must be bonded into the root canal sufficiently strongly and to a sufficient depth to prevent it becoming loosened, for instance due to the very powerful leverage forces that may be applied on to the post by normal biting on to the cap.

In order to promote firm bonding of the post within the cavity, it is known to provide the lower portion of the post with a roughened, sand-blasted, surface. The resultant notches or recesses formed by the sand blasting are very small and will open outwardly in a direction substantially perpendicular to the axis of the post. Also a particular form of post (sold under the trade name Parapost) has a series of parallel grooves each of which extend substantially around the lower portion. The separation of each of these grooves is normally at least 1 mm. In order that the angles defined by the side walls of each groove are such as to promote bonding, an inevitable consequence of having this spacing of at least 1 mm is that each groove has a significant depth, relative to the diameter of the post.

Other posts having a few widely spaced grooves are shown in EP 260446. An extra disadvantage of widely spaced grooves is that the results are greatly influenced by the precise number of grooves within the cavity.

Normal posts, like the "Parapost", are of uniform diameter. However it is also known for the post to be tapered, so that its diameter decreases downwardly. This has the advantage that the post can extend further into the canal, so as to spread the leverage forces more uniformly. If a non-tapered post were to extend the same distance, the canal would have to be drilled out more extensively to receive the broader end of the post and this increases the risk of the tooth fracturing when strong leverage forces are applied.

It is also known to sand blast the tapered portion of a post in order to maximise adhesion between the tapered portion and the bonding agent that secures the post within the cavity. Although this can give improved adhesion between the bonding agent and the post, it does not affect the adhesion between the bonding agent and the inner surface of the cavity.

In GB 2117641 a dental post assembly includes a coarsely screw threaded post which is inserted by rotating so that the spiral bites into the walls of the root canal. This method again, places stress on the root of the tooth and imposes the risk of fracturing the remaining dental root. In addition, the dental post disclosed in GB 2117641 includes a bush screw-threadedly engaged with the post on a fine screw thread so that the bush can be adjusted lengthwise. Another screw fitting system is shown in Reissue U.S. Pat. No. 31948.

With all the existing methods there is either the risk of stressing the tooth by screwing or the risk that the adhesion between the cement and the cavity may fail, in which event the crown will become loose, and the desired cosmetic effect of an artificial tooth replacement is lost.

It would be desirable to devise a method of fixing a crown in which the firmness of the post did not depend primarily on the strength of adhesion between the cement and the inner surface of the canal. It would also be desirable to provide a reamer and a post suitable for use in the method. It would also be desirable to provide a post that could extend deeply into the canal without increasing the risk of fracturing the tooth and yet which can be bonded extremely securely into the cavity. The present invention provides various ways of achieving these and other objectives.

In the present invention, there is provided a method of securing a dental crown, that should be cosmetically desirable, above a pre-prepared dental root canal comprising using a dental post that has an upper portion to which a dental crown may be secured, a lower portion that can be secured within the dental root canal and that extends downwardly from the upper portion, and a plurality of notches in substantially the entire length of the surface of the lower portion. The method comprises securing the lower portion of the dental post inside the dental root canal and securing the crown to the upper portion and is characterised in that a plurality of projections that extend downwardly and inwardly have been preformed in the walls of the dental root canal and the lower portion is positioned within the canal and defines an annulus between the post and the wall of the pre-prepared root canal, the annulus is filled with a curable cement and the cement is cured to secure the lower portion in the canal.

It is particularly preferred that the lower portion of the post should include a tapered portion that leads to the end of the post since this permits the post to be fitted more deeply into the root canal without the need for drilling out such a wide canal near the base of the canal. The tapered portion usually extends over at least about a quarter, and usually at least about half of the length of the lower portion and frequently the entire lower portion is tapered. The diameter of the tapered bottom end of the lower portion is generally less than about three quarters, often about one fifth to one half or even two thirds, of the diameter of the top of the lower portion.

The notches extend over substantially the entire length of the lower portion and so extend over the tapered portion.

Preferably the notches in the lower portion open upwardly and outwardly since they then oppose the projections in the wall of the canal and this gives best cementing. However the benefit of these projections can also be obtained, to some extent at least, if the notches in the post face outwardly substantially perpendicular to axis or even downwards. The angle with which they project downwards should preferably be small, e.g., below 30° from the line that is perpendicular to the axis.

As a result of the projections in the surface of the dental root canal, the cement between the post and the canal wall is trapped between notches in the post that open outwardly (and preferably upwardly) and projections in the wall of the canal that extend inwardly and downwardly. The securement of the post in the cavity therefore depends to a large extent on the shear strength of the cement rather than on the adhesive strength of the cement to the post and, especially, to the canal wall. This can result in the post being held in the canal much more securely. It also permits a much wider choice of cements since adhesion is not solely dependent on its adhesiveness to the surface of the canal cavity. A wide variety of dental cements can be used.

The projections in the wall of the root canal can be discrete projections but preferably each is a ridge that extends around part or all of the canal wall, each ridge being defined by a lower ridge face and an upper ridge face wherein the lower ridge face is inclined at a greater angle to the axis of the canal, and is shorter than, the upper ridge face, the ridges preferably being substantially parallel to one another.

The ridges or other projections in the canal wall can have very small dimensions, both as regards pitch and, optionally, depth, for instance below 0.3 mm as proposed below for the notches. However, satisfactory results can be obtained when the pitch of the ridges (i.e., the axial spacing between the peaks of adjacent ridges) is substantially greater than the pitch of the notches. For instance the ridges or other projections typically have a pitch of from 0.2 to 3 mm, often 0.2 to 1 mm.

The cavity can be drilled, and the projections formed, using known dentistry reamers. For instance a reamer having a single cutting head can be used to cut into the wall of the canal to form each projection inturn. However this is inconvenient in practice and preferably the projections are formed using a novel dental reamer designed specifically for the formation of the parallel ridges.

A novel dental reamer for forming a profiled cavity in a tooth, for instance in a root canal cavity, comprises an elongated body, means for mounting the body for drilling rotation, and a cutting head mounted on the elongated body distant from the mounting means for rotation with the body, and in this reamer the cutting head is elongated and has a plurality of cutting elements spaced along its length and these are shaped to profile into the wall of the cavity to define the plurality of inwardly and downwardly projecting ridges that each extend around part or all of the cavity and that are arranged substantially parallel to one another. The number and spacing of cutting elements will be chosen according to the desired spacing of the ridges in the cavity wall.

The cutting head may extend along the entire length of the elongated body, but generally it is mounted only at one end. The head can be cylindrical, but is preferably tapered. The cutting elements are usually outwardly extending teeth.

The cutting head of the reamer may be designed such that it can be used for simultaneously drilling the cavity and forming the ridges or it can be such that the cavity is drilled to substantially the desired size by a conventional drill and the novel reamer is then used solely for removing sufficient of the tooth to define the ridges. The dimensions of the reamer will be sufficiently small that it can be used for forming a cavity in a tooth and will be selected according to the size of the cavity that is to be formed in the tooth. Usually it is of a size suitable for profiling a root canal. It can be made of materials that are conventional for dental reamers.

The novel reamer is usually tapered along part or all of its length, especially when it is to be used for forming a tapered cavity for use with a tapered post. The angle of the taper can be for instance about 3° to 15°, often about 3° to 10°, and an angle of about 5° is often suitable for drilling a canal cavity in the invention.

The pre-prepared root canal preferably has a sufficiently wide diameter along its length that the post is a loose sliding fit and defines a continuous narrow annulus. Thus, since the post is preferably tapered, the canal also is preferably tapered in a generally similar configuration, and conveniently the reamer has a similar taper. An advantage of the loose sliding fit is that it eliminates the need for, or risk of, screwing the post into the canal. Thus the post is preferably inserted into the prepared canal by pushing, substantially without screwing. However the post can make a screw fit with parts at least of the canal wall, for instance the projections or even the entire length of the wall. It is highly desirable that the screw fit should be too weak, by itself, to secure the post (because of the risk of stressing the tooth as a result of screw fitting) but the combination of a very weak screw fit and the cement can give desirable results. Thus the annulus between the post and the canal wall does not have to extend continuously along the length of the post but can instead be interrupted by contact points between the post and the canal wall.

Various shapes and designs of upper portions for dental posts are known and can be used in the invention. For instance there may be a few relatively large, often square cut, grooves to permit fixing of the crown in conventional manner.

The crown can be any suitable crown or cap that is capable of being secured to the upper portion of the post. Preferably the surface of the upper portion, like the surface of the lower portion, carries a plurality of notches that open outwardly, but the notches in the upper portion preferably extend downwardly.

A novel dental post has an upper portion to which a dental crown may be secured and a lower portion that can be secured within a dental root canal and that extends downwardly from the upper portion, a plurality of notches that open outwardly and upwardly are formed in the surface of substantially the entire lower portion and a plurality of notches that open in the opposing direction are formed in the upper portion for securing the dental crown to it. Preferably the lower portion is tapered, as described above.

The notches in the lower portion of the post preferably open upwardly and outwardly in order to maximise the resistance of the post to an upward pull, and the notches in the upper portion preferably open in the opposing direction in order to maximise the resistance of the dental crown to an upward pull.

The notches in the post can be a series of discrete notches but preferably they are a plurality of grooves that, within each portion, are generally substantially parallel. Each groove extends substantially around the lower portion or substantially around the upper portion respectively. The grooves of the lower portion preferably are each defined by an upper side wall and a lower side wall that is inclined at a greater angle to the axis of the lower portion, and is shorter than, the upper side wall. Each groove in the upper portion is preferably defined by a lower side wall and an upper side wall that is inclined at a greater angle to the axis of the upper portion, and is shorter than, the lower side wall.

The provision of the notches in the surface of the lower portion of the post must not result in substantial and unacceptable reduction in the strength of the post. If the number of grooves or other notches is relatively small each may have to be so deep, in order to give satisfactory bonding strength, as to risk weakening the post and so preferably there are a large number of small notches. For instance the pitch of the grooves or other notches (i.e., the axial spacing between the bases of adjacent grooves or other notches) will generally be considerably less than about 1 mm and usually less than about 0.5 mm. The grooves in the upper portion of the dental post may have similar dimensions.

The pitch of the grooves is preferably below about 0.3 and generally below about 0.2 mm. It must not be too small, as otherwise some bonding agents may not be able to migrate into the recesses of the grooves, and so normally is at least about 0.05 mm and generally at least about 0.1 mm. A pitch from about 0.1 to 0.2 mm is generally preferred. The depth of each groove should also normally fall within the ranges described above for the pitch, and usually the depth of each groove is quarter to one times the pitch.

As a result of the provision of these very small grooves or other notches it is possible to provide a large number of them (typically 20-50) in the surface of the lower portion substantially without weakening that portion, and yet the provision of this large number of grooves allows greatly improved adhesion with the cement. A particular advantage of having a large number of small grooves is that a small decrease in the number of grooves, for instance due to shortening the post to fit any particular tooth, has very little effect upon the bonding potential with the post. Accordingly the post can be set over a range of depths with very little variation in the strength of the fitting. If there were only a few larger grooves then the length of the post may be dictated by the need to avoid cutting off part of the post that carries one of the grooves. This is a problem with posts of the type shown in EP 260446.

Although the grooves can be spaced apart, it is generally preferred that the lower and upper side walls of one groove merge directly into the upper and lower side walls respectively of the adjacent grooves. Thus there is preferably substantially no cylindrical surface between adjacent grooves.

As indicated above, it is desirable to avoid stressing the tooth by screw fitting of the post. Accordingly, although the plurality of substantially parallel grooves could be provided by one or more conventional screw threaded grooves (i.e., right-handed helical grooves extending helically along the lower portion), this is rather undesirable as the dentist may be tempted to mis-use the post and screw it in with a conventional clockwise drive. Preferably therefore the grooves are designed to avoid this. They can be left-handed helical grooves (since normal drills will not screw such a post into a canal) or they can be provided by a series of independent grooves.

A novel dental post has an upper portion to which a dental crown may be secured and a lower portion that can be secured within a dental root canal and that extends downwardly from the upper portion, and a plurality of substantially parallel grooves are formed in the surface of substantially the entire length of the lower portion either as left-handed helical grooves or as independent grooves, and the pitch of the grooves is not more than about 0.5 mm. Preferably each groove is defined by an upper side wall and a lower side wall that is inclined at a greater angle to the axis of the lower portion, and is shorter than, the upper side wall. Preferably the pitch of the grooves is as described above and the post is tapered, as described above.

It is desirable for the grooves to be a left-handed helix or independent, rather than a conventional helix, as in much of the prior art, because it is not necessary (and indeed is generally undesirable) to screw the post into the cavity and these designs (especially independent grooves, which are preferred) eliminate any tendency to screw fitting. This therefore constitutes a significant advantage over, for instance, the screw fitting system of GB 2,117,641.

The dental post can be formed from conventional materials such as special non-toxic steels of the type that are conventionally used or, preferably, titanium.

The post is preferably provided with means for preventing rotation of it within the root canal cavity. Such means are well known and may include an axially extending projection or recess along part or all of the post.

The process and posts of the invention are of particular value for fitting a dental crown in a tooth having a single root, i.e., a front tooth, in which event a single post is used in that tooth. However, the invention can also be used in multi-post systems, for instance in back teeth. The post is generally supplied as a straight post, but can be bent if desired in conventional manner.

Preferably one (or more than one) reamer is supplied as a kit with a plurality of posts suitable for use in the method of the invention, preferably the novel posts as defined above.

The invention is now described with reference to the accompanying drawings in which:

FIG. 1 is a diagrammatic representation of a tooth that has been capped by using a dental post;

FIG. 2 is a side view of a post according to the invention;

FIG. 2A is a side view of the lower portion of the post of FIG. 2 in which the grooves are left-handed helical grooves;

FIG. 3 is a cross-section on the line III—III in FIG. 2;

FIG. 4 is an enlarged longitudinal cross-section of the post of FIG. 2;

Figure 5:
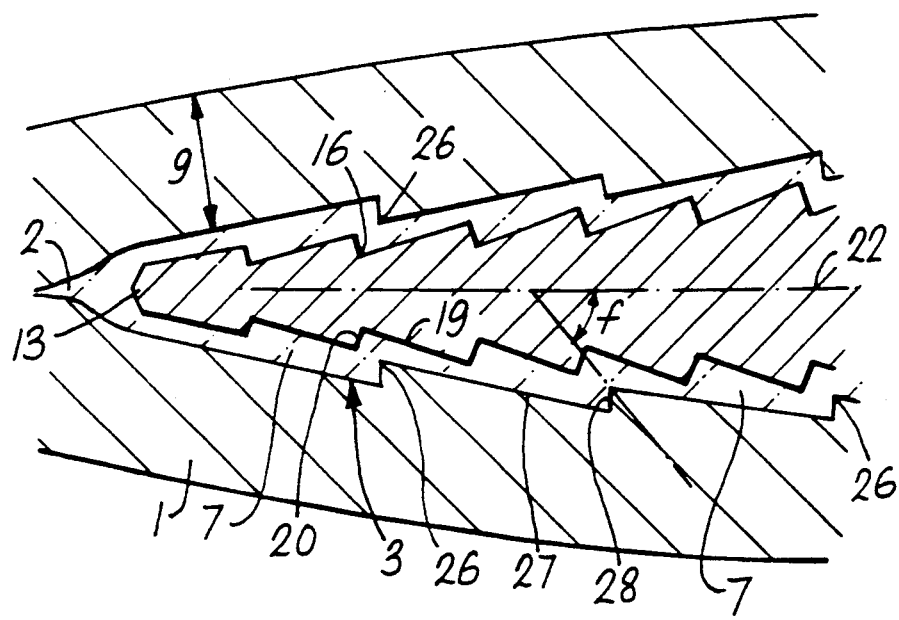
FIG. 5 is an enlarged diagrammatic cross-section showing the post and the profiled canal cavity.

Referring to FIG. 1, tooth root 1 has a root canal 2 which has been drilled to provide a cavity 3 into which has been fitted the lower portion 4 of a post 5 having an upper portion 6. There is an annulus 7 between the lower portion 4 and the cavity 3. The post is bonded into the cavity by means of suitable cement that fills the annulus 7 and that provides a bond between the surface of the post and the surface of the cavity.

The cement for this purpose may be any of the cements that are suitable for bonding a post into a root canal such as zinc phosphate cements, glass ionomer cements and epoxy cements such as those sold under the trade name "Araldite".

A crown 8 is secured over the upper portion 6 of the post by conventional tooth build-up material for instance amalgam or resin composite, for instance one based on an epoxy resin such as Araldite. Means (not shown) may be provided for preventing rotation of the crown relative to the tooth. These can include pins or other fasteners between the crown and the tooth or may rely upon the use of two posts (for back teeth) or may include a longitudinal groove or other means in the post for preventing rotation of the post relative to the tooth and for preventing rotation of the cap relative to the post.

Referring to FIG. 2, the upper portion 6 extends from the upper end 10 cylindrically to a point 11. The lower portion 4 extends cylindrically from point 11 to point 12, where the post begins to taper, to the tapered tip 13. There are diametrically opposed longitudinal grooves 14 extending along most of the length of the post, in order to prevent rotation of it. The remainder of the surface of the post is profiled with transverse grooves shown in more detail in FIG. 4. These grooves extend downwardly between points 10 and 11 and extend upwardly between points 11 and 13.

The transverse grooves are parallel upwardly facing grooves 16 (in the lower portion) and downwardly facing grooves 17 (in the upper portion). Each groove serves as a notch that opens outwardly, in the sense that the notch faces outwards and has a wide mouth 18 to allow easy access of bonding agent to the surface of the post. Each notch or groove is defined by an upper side wall 19 and a lower side wall 20. The notches face upwardly in the sense that the angle formed between a median line 21 (drawn between the surfaces 19 and 20) and the axis 22 of the post is at an angle c which is less than 90°. Each lower side wall 20 is shorter than its corresponding upper side wall 19 and is at an angle b to the axis 22 that is greater than the angle a between the upper side wall and the axis 22.

In the upper portion of the post, the angles and dimensions are reversed. Thus the lower wall 23 of each groove is longer than the upper wall 24 and the median line 25 extends at an angle d to the axis where d is greater than 90°.

Instead of regarding the walls 19 and 20 and the walls 23 and 24 as defining grooves or notches, they can of course alternatively be regarded as defining projections.

It is normally desired that the pitch (i.e., the distance e between the base of one groove and the base of the next groove) should be very small, typically around 0.15 mm. Although it is possible to have a cylindrical surface between the lower wall 20 of one groove and the upper wall 19 of the next groove, generally these two walls merge into one another, as shown in FIG. 4. In typical constructions the angle a is between about 25° and 60°, often about 30° to 50°, whilst the angle b is generally about 60° to 90°, typically about 70° to 90°. In some instances it can be desirable for b to be up to, for instance, about 105°. Generally there should be a difference of at least about 20° between b and a. The angle c is usually between about 30° and 85°, generally about 50° to 80°. The angle d is generally between about 95° and 150°, often between 100° and 130°. The depth of each groove typically is from 0.02 to 0.2 mm.

Referring to FIG. 5, the root canal 2 is drilled out to form a cavity having a profiled inner wall 3. This cavity has a plurality of projections 26 that extend inwardly and downwardly from the cavity wall. Each projection conveniently is a ridge that is defined by a lower ridge face 27 and an upper ridge face 28 that is inclined at a greater angle to the axis 22, and is shorter than, the lower ridge face 27. Thus the angles and relative lengths may be opposite those for the notches in the lower portion of the post, as discussed in connection with FIG. 4. The ridge extends downwardly in the sense that a median line 29 makes an angle f with the axis 22, where f is below 90°, for instance as described above for angle c.

Instead of regarding the profiling as the provision of projections 26 it can, of course, be regarded as the provision of notches, formed between adjacent projections.

The pitch of the grooves defined by adjacent projections can be the same order of magnitude as described above for the post or can be larger. Often the pitch of the ridges cut into the cavity is 2 to 5 times the pitch of the grooves in the post.

The annulus 7 is the gap formed between the post and the wall of the canal and may be a continuous annulus or may be a discontinuous annulus, for instance being interrupted by inter-engagement between the projections 26 and the post. The cavity may be substantially filled with cement before insertion of the post or the bonding agent may be introduced with or after the post. The cement can be a conventional dental cement that cures after insertion. The combination of the cured cement with the notches 16 and the projections 26 means that the upward force necessary to pull the post upwardly is very much greater than if the bonding relied solely upon adhesion between a conventionally profiled canal cavity and a sand-blasted post. For instance the force required to remove a post typically is of the order of 3 kilos whereas in the invention it may be 5 to 10 times as much, or more.

Whenever a post is fitted in a tooth, a potential point of weakness is created if the minimum wall thickness of the tooth becomes too low. Since the tooth is itself tapered the provision of a cylindrical cavity, as is required for a cylindrical post, means that the thickness g at the tip 13 of the post may be undesirably reduced unless tho post is shorter. However if the post is shorter the tip 13 does not extend so far down into the tooth and the bonding of the post into the tooth may be inadequate to resist some leverage forces. By the invention, the tip 13 can extend deeper into the tooth whilst ensuring that the distance g is sufficient to minimise the risk of fracturing of the tooth.

Figure 6:
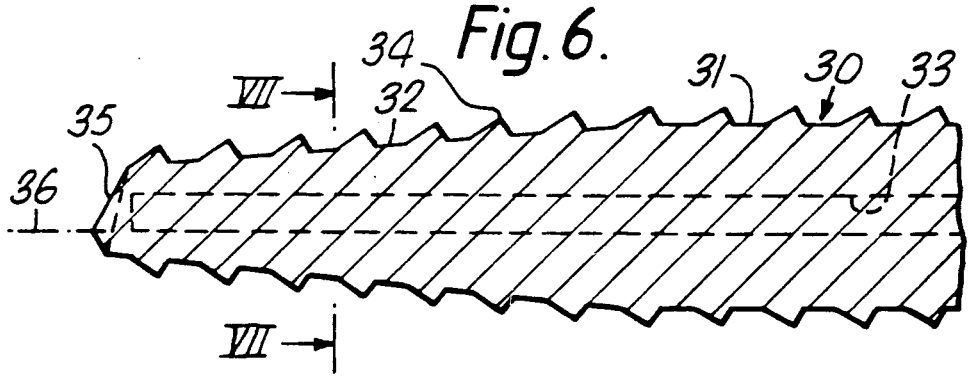
FIG. 6 is a longitudinal cross-section of a dental reamer suitable for forming the profile shown in FIG. 5.

The profiling shown in FIG. 5 can conveniently be achieved by use of a profiling tool or reamer that can have a conventional elongated body and mounting for fixing to a drill but which is provided with a novel type of cutting head, as shown at 30 in FIG. 6. The cutting head is shown as having a substantially cylindrical portion 31 and a tapered portion 32 leading to a tapered end 35. In some instances the entire head can be tapered whilst in other instances the entire head can be cylindrical. The head is provided with a plurality of spaced apart cutting elements that comprise teeth 33 at the leading edge (during rotation) of ridges 34 that extend around part of the radius of the cutting head. The profiling of the ridges 34, and thus of the teeth 33, will be chosen so as to match the desired profile between the projections 26 in the tooth. The spacing between adjacent ridges will be the spacing that is required between adjacent projections 26, typically around 0.5 to 1.5 mm. Normally there will be at least 3 and often 5 to 20 spaced apart cutting teeth along the length of the cutting head.

Figure 7:
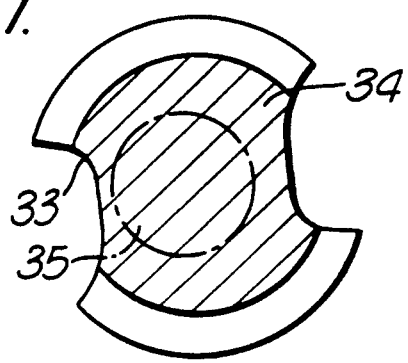
FIG. 7 is an enlarged cross-section on the line VII—VII in FIG. 6.

The construction of the teeth 33 and the remainder of the cutting head can be such that it is conveniently used for the initial drilling of the root canal or can be such that the canal is drilled approximately to the desired size using a conventional drill and can then be profiled by the use of the described cutting head. The diameter of the cutting head is normally substantially less than the diameter that is desired in the cavity, in which event the cutting head has to be moved around the walls of the cavity while rotating, and for instance may be rotated eccentrically within the cavity. This can be achieved by manual movement of the axis of the cutting head along a circular path but a more convenient way of achieving this is to rely on the tip 35 of the cutter being shaped as an eccentric point, as shown in FIGS. 6 and 7. The axis 36 of the cutter is shown in dashed line. The effect of the eccentric point on reaching the bottom of a pre-drilled cavity, is to cause the axis of the cutter to follow a circular path as the cutter rotates and this forces cutting edges against the cavity wall so as to create the desired undercuts, for instance as shown in FIG. 5.

I claim:

1. A method of securing a cosmetically desirable dental crown above a pre-prepared dental root canal using a dental post wherein the post has
    an upper portion to which the dental crown may be secured,
    a lower portion that can be secured within the dental root canal and that extends downwardly from the upper portion and
    a plurality of notches in substantially the entire length of the surface of the lower portion,
    and in which the method comprises forming a plurality of projections that extend downwardly and inwardly in the walls of the dental root canal, positioning the lower portion of the post within the canal and thereby defining an annulus between the post and the wall of the pre-prepared root canal, filling the annulus with a curable cement and curing the cement to secure the lower portion in the canal, and securing the crown to the upper portion.

2. A method according to claim 1 in which the lower portion is tapered to a tapered end.

3. A method according to claim 1 or wherein the plurality of notches in the lower portion of the dental post open upwardly and outwardly in the surface of the lower portion.

4. A method according to claim 1 wherein the notches are a plurality of substantially parallel grooves and each groove is defined by an upper side wall and a lower side wall that is inclined at a greater angle to the axis of the lower portion and is shorter than, the upper side wall and the pitch of the grooves is not more than 0.5 mm.

5. A method according to claim 4 wherein the grooves in the lower portion of the dental post are selected from the group consisting of independent grooves and left-handed helical grooves.

6. A method according to claim 1 in which the post is pushed into the canal substantially without screwing.

7. A dental post having
    an upper portion to which a dental crown may be secured and a lower portion that can be secured within a dental root canal and that extends downwardly from the upper portion and that has a plurality of substantially parallel grooves formed in its surface over substantially its entire length,
    characterised in that the grooves are selected from the group consisting of independent grooves and left-handed helical grooves, and the pitch of the grooves is not more than 0.5 mm.

8. A dental post according to claim 7 wherein each groove is defined by an upper side wall and a lower side wall that is inclined at a greater angle to the axis of the lower portion, and is shorter than the upper side wall.

9. A post according to claim 8 in which the upper and lower side walls of each groove merge with the lower and upper side walls respectively of adjacent grooves.

10. A post according to claim 7 wherein the pitch of the groove is below 0.3 mm and is at least 0.05 mm.

11. A post according to claim 7 in which the lower portion is tapered to a tapered end.

12. A post according to claim 7 in which the post is tapered over at least the lowermost half of the lower portion to a diameter below three quarters of the diameter of the top of the lower portion.

13. A dental post having
    an upper portion to which a dental crown may be secured and
    a lower portion that can be secured within a dental root canal and that extends downwardly from the upper portion
    characterised in that a plurality of notches that open upwardly and outwardly are formed in the surface of substantially the entire length of the lower portion and a plurality of notches that open in the opposing direction are formed in the upper portion for securing the dental crown to the upper portion wherein the plurality of notches of the lower portion are a plurality of substantially parallel grooves and each groove is defined by an upper side wall and a lower side wall that is inclined at a greater angle to the axis of the lower portion and is shorter than the upper side wall, and the pitch of the grooves is not more than 0.5 mm.

14. A post according to claim 13 in which the upper and lower side walls of each groove merge with the lower and upper side walls respectively of adjacent grooves.

15. A post according to claim 13 wherein the pitch of the groove is below 0.3 mm and is at least 0.05 mm.

16. A post according to claim 13 in which the lower portion is tapered to a tapered end.

17. A post according to claim 13 in which the post is tapered over at least the lowermost half of the lower portion to a diameter below three quarters of the diameter of the top of the lower portion.

* * * * *